Figure 1:
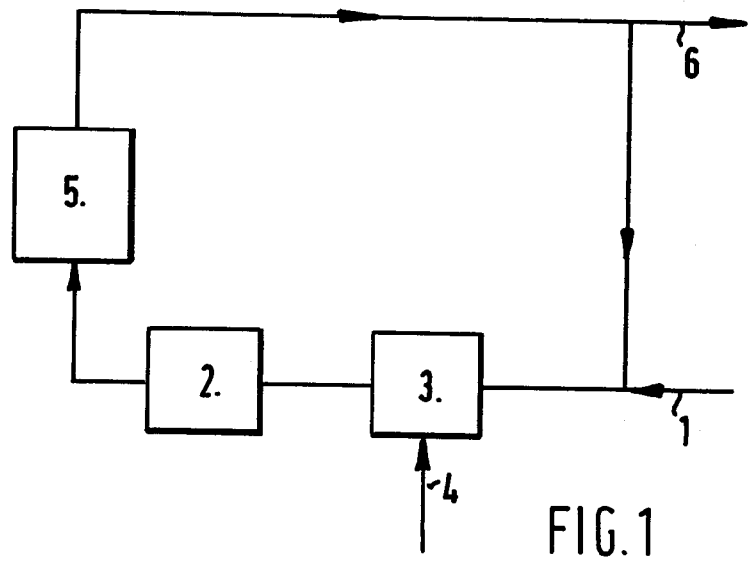

United States Patent [19]

Akred et al.

[11] 4,226,796

[45] Oct. 7, 1980

[54] SULPH(ON)ATION PROCESS

[75] Inventors: Brian J. Akred; Alan J. Lambie; John Maden, all of Whitehaven, England

[73] Assignee: Albright & Wilson Limited, West Midlands, England

[21] Appl. No.: 857,807

[22] Filed: Dec. 5, 1977

Related U.S. Application Data

[63] Continuation of Ser. No. 686,433, May 14, 1976, abandoned.

[51] Int. Cl.² .................. C07C 141/04; C07C 143/24
[52] U.S. Cl. .......................... 260/459 R; 260/505 S; 260/505 E; 260/458 R
[58] Field of Search ............ 260/505 E, 505 S, 459 R, 260/458

[56] References Cited

U.S. PATENT DOCUMENTS

| 2,831,020 | 4/1958 | Norwood et al. | 260/505 E |
| 2,843,626 | 7/1958 | Gebelein et al. | 260/505 S |
| 2,889,361 | 6/1959 | Brooks | 260/505 E |
| 3,232,976 | 2/1966 | Lohr | 260/505 S |

OTHER PUBLICATIONS

Rose, "The Condensed Chem. Dict.," 5th Ed. (1956), p. 943.

*Primary Examiner*—Alan Siegel
*Attorney, Agent, or Firm*—Frishauf, Holtz, Goodman & Woodward

[57] ABSTRACT

Sulph(on)ation of organic feedstocks is performed with undiluted sulphur trioxide in a recycle loop reactor in which the feedstock is diluted with its recycled sulph(on)ation product, contact of the feedstock and sulphur trioxide occurs under conditions of turbulent flow and the recycle ratio is high.

19 Claims, 2 Drawing Figures

SULPH(ON)ATION PROCESS

This is a continuation, of application Ser. No. 686,433, filed May 14, 1976 now abandoned.

The present invention relates to a sulph(on)ation process.

When a sulph(on)atable organic compound, e.g. an aromatic compound such as benzene or a fatty alcohol such as lauryl alcohol is sulph(on)ated by sulphur trioxide, there is a considerable evolution of heat, which, if associated with local high concentrations of sulphur trioxide in the reaction mixture, may give rise to a heavily discoloured reaction product.

In this Specification the terms "sulph(on)ated", "sulph(on)atable" and "sulph(on)ation" means sulphonated, sulphonatable and sulphonation, or sulphated, sulphatable and sulphation, depending on the nature of the compound reacted; thus aromatic hydrocarbons are sulphonated, but fatty alcohols are sulphated. In order to produce light coloured sulph(on)ated products, such as aromatic sulphonic acid reaction products for use, e.g. as surface active agents or hydrotropes or fatty alcohol sulphate reaction products for use, e.g. as surface active agents, it is usual to moderate the effects of the heat of reaction by diluting the sulphur trioxide, either with an inert gas, e.g. to a 5% concentration in dry air, or with an inert liquid diluent, e.g. a chlorinated hydrocarbon or liquid sulphur dioxide. The need for the gaseous or liquid diluent introduces problems of purification of the diluent before the reaction and removal thereafter and problems in use. Thus gaseous diluents have to be dried before use and separated from the reaction product after the reaction without entrainment of product, unreacted sulph(on)atable compound and/or liquid diluent. The presence of gaseous diluents in the liquid reaction medium means that they are more difficult to pump than liquid phases only. Liquid diluents have to be separated from the reaction product. It has also been proposed to use the sulphur trioxide gas as such and undiluted but under externally applied reduced pressure. It is known to react the sulph(on)atable compound with liquid sulphur trioxide in a complicated apparatus in which the sulphur trioxide is directed at an organic compound present on the surface of at least four moving impeller blades which are close to heat transfer surfaces. The reacting mixture of organic compound and sulphur trioxide is sheared between the impeller blade and the heat transfer surface to reduce the temperature. Finally, it is known to sulph(on)ate sulph(on)atable compounds with a sulphur trioxide/air mixture in a loop reactor with removal of one fifth to one thirtieth of the reaction product and recycle of the rest. It is suggested in a further document that undiluted gaseous sulphur trioxide could be used in a continuous loop process but no details are given.

We have now found we can prepare a sulph(on)ated product by a process with undiluted liquid or gaseous sulphur trioxide in a simple apparatus with a loop in which the organic feedstock is diluted with its recycled sulph(on)ated reaction product, contact between organic feedstock and sulphur trioxide occurs under conditions of turbulent flow and the amount of recycle is very high. The process has the advantage of requiring no diluent for the sulphur trioxide and in the case of alkyl benzene feedstocks often gives light coloured products.

The present invention provides a process for sulph(on)ating a sulph(on)atable organic feedstock, which is preferably an aromatic compound or a fatty alcohol of 8–18 carbon atoms, which comprises passing undiluted sulphur trioxide in liquid or gaseous form into a reactant liquid comprising the organic feedstock and its sulph(on)ated derivative to give a reaction mixture, the liquid being in a condition of turbulent flow at the point of contact of the sulphur trioxide and liquid and thereafter in the zone of reaction of sulphur trioxide and liquid, cooling the reaction mixture before and/or after removing a portion of the reaction mixture as sulph(on)ated product, the weight ratio of reaction mixture removed to the remainder of reaction mixture being in the range 1:40 to 1:2000, adding further organic feedstock to the remainder of the reaction mixture to compensate for that removed as product and to reconstitute the reactant liquid and recycling it for contact with more sulphur trioxide.

The compounds which may be sulphonated in the process of the invention, include aromatic compounds of 6–36 carbon atoms free from groups unstable under the reaction conditions, e.g. free amino groups. Examples are benzene and alkyl benzenes having 1–3 alkyl groups, each of 1–15 carbon atoms, such as alkyl benzenes with 1–3 alkyl groups, each of 1 to 5, especially 1 to 3 carbon atoms, e.g. toluene and the 3 isomers of xylene, and monoalkyl benzenes in which the alkyl group contains 8–15 carbon atoms, e.g. dodecyl benzenes, such as benzene with a linear dodecyl or propylene tetramer side chain. The aromatic compound may have one or two substituents which are halogen atoms, such as chlorine or bromine (as in chloro toluenes), hydroxyl groups (as in phenol) or carboxylic groups (as in benzoic acid); the aromatic compound may have one nitro or one sulphonic acid substituent. The total number of substituents in any benzene ring is usually not more than 3. The naphthalene equivalents of the above compounds, e.g. naphthalene itself may also be sulphonated. Other classes of sulphonatable organic feedstocks are olefins, e.g. those of 8–20 carbon atoms, such as dodec-1-ene, hexadec-1-ene and octadec-1-ene, or random unsaturated hexadecene or vinylidene olefins, and fatty acids, e.g. those of 8–20 carbon atoms such as lauric and stearic acids, as well as olefinic acids, e.g. of 3–20 carbon atoms, preferably 4–18 carbon atoms such as maleic, fumaric and oleic acids.

Examples of sulphatable organic feedstocks are alcohols, preferably fatty ones of 8–20 carbon atoms, such as lauryl, cetyl and stearyl alcohols and mixtures thereof, including mixtures such as are commercially available with a larger proportion of one of these alcohols and smaller amounts of other alcohols. The reaction products of these fatty alcohols with ethylene oxide or propylene oxide which usually contain 1–10 of structural units derived from the oxide may be sulphated. Alkyl phenols with, e.g. 1–12 carbon atoms in the alkyl group, and the reaction products of 1 mole of them with, e.g. 1–10 moles of ethylene oxide or propylene oxide, fatty acid alkanol amides, e.g. with 8–18 carbon atoms in the fatty acid part, e.g. that derived from lauric acid and 2–12 carbon atoms in the alkanolamide part, e.g. that derived from mono or di or tri ethanolamine, and the reaction products of 1 mole of the fatty acid alkanolamides with e.g. 1–10 moles of ethylene oxide or propylene oxide may also be sulphated.

Preferably however, the sulph(on)atable compound is benzene or an alkyl benzene as defined above or a fatty alcohol. The sulphur trioxide is preferably in gaseous form.

The sulph(on)ated products may be used in detergent compositions.

An essential feature of this invention is that the sulphur trioxide and organic feedstock are contacted when the liquid containing the feedstock is in a condition of turbulent flow, preferably with an apparent Reynolds Number of at least 2,000 e.g. at least 3,000, usually 3,000–18,000 such as 3,000–10,000 or 10,000 to 15,000. The Reynolds Number can be greater than 18,000 but the higher values become progressively uneconomic. The apparent Reynolds Number is calculated on the assumption that there is no gas phase present, i.e. in the case of the use of gaseous $SO_3$ its volume is neglected.

Turbulence can be achieved with a variety of mixers, e.g. those described in "Chemical Engineers Handbook", Ed. R. H. Perry and C. H. Chilton, McGraw Hill Book Co., New York, 5th edition, 1973, Section 21, pages 4–8, such as jet mixers, orifice plate mixers, "Kenic" mixers nozzle mixers and centrifugal pumps and mechanically agitated mixers, such as "Silverson" mixers (whether the rotors in the mixer are operated or not), centrifugal pumps and mixers such as described in British Patent Specification No. 1052976. In each case the input pipe for the sulphur trioxide is positioned such that its end is in a region of turbulence in the mixer.

On grounds of capital, operating and repair costs, the mixer is preferably a static one with no moving parts. Examples of such mixers are orifice plate, "Kenic", venturi and jet mixers, as well as arrangements in which the inlet pipe for the sulphur trioxide and the pipes carrying the recycled reaction liquid containing the feed stock are so disposed that, with the aid of baffles, if necessary or desired, there is the necessary turbulent flow under the conditions of temperature, nature of feedstock and flow rates operating in the process. Especially important are orifice plate mixers which comprise a plate disposed across the reaction liquid flow with at least one axial orifice, through which the liquid passes, the act of passage causing production of turbulent flow in the orifice upstream and downstream of the orifice. Preferably the sulphur trioxide is passed through a pipe whose exit is in the turbulent region in the vicinity of the orifice, whether upstream or downstream of the orifice, or in the orifice itself. The sulphur trioxide may be passed into the turbulent region from a direction parallel with e.g. coaxial with the bulk direction of flow of the reaction liquid or may be passed from a direction substantially normal to the bulk direction of flow. The inlet pipe for the sulphur trioxide can pass through the orifice as shown in British Patent Specification No. 975914, or with the inlet pipe surrounded by the reaction liquid upstream of the orifice and the end of the inlet pipe in the orifice instead of passing through it. Alternatively, the inlet pipe can pass from outside the line carrying the reaction mixture directly into the turbulent region downstream of the orifice, usually normal to the bulk direction of flow of the reaction liquid.

The turbulent flow is achieved by use of the mixer and also in the loop circuit through which the liquid flows there is a pump; the requirement for turbulent flow necessitates a pump operating at a high pumping rate. The turbulent flow occurs in the mixer and in the reaction zone wherever unreacted sulphur trioxide contacts feedstocks (or sulph(on)ated derivatives thereof) and reacts with it. Most pumps and heat exchangers for cooling the reaction mixture keep turbulent a liquid fed thereinto in a state of turbulent flow. Fixed pressure pumps, e.g. centrifugal pumps are preferred though any other type of pump capable of a high pumping rate may be used. It is possible for the mixer also to act as a pump, e.g. with the Silverson mixer with the rotor operating, but preferably the mixer and pump are separate. Light colour sulphonates from alkyl benzenes can best be produced if the liquid mixes with the sulphur trioxide before passing through the pump rather than afterwards, i.e. the mixer is at the inlet side of the pump rather than the outlet side. The recycle loop system also contains a heat exchanger as cooler, and inlet for feedstocks and outlet for reaction mixture. Preferably the cooler is between the mixer and outlet in the direction of liquid flow. Thus preferably the sulph(on)ation occurs in a recycle loop reactor through which is pumped the reaction liquid and mixture, the reactor having in the direction of flow of the reaction mixture and liquid, an inlet for feedstock, a mixer giving turbulent flow into which sulphur trioxide, preferably in gaseous form is passed, a pump, a heat exchanger as cooler and an outlet for reaction mixture. The reaction liquid and mixture are preferably in a state of turbulent flow in the mixer, pump and heat exchanger and may be throughout the loop. The sulphur trioxide and feedstock are passed into the loop continuously and the sulph(on)ation product is removed continuously.

The temperature of the liquid as it enters the mixer before reaction with sulphur trioxide is primarily governed by the need to control the viscosity of the liquid, the lower limit being that to maintain a viscosity such that there is turbulent flow, the upper limit being preferably 150° C., and pressure being placed on the system if necessary to stop volatilization of the organic compound at the liquid temperature. Preferably the temperature of the liquid is 0°–80° C., and especially 10°–60° C. The use of high temperatures may tend to give greater discolouration in the sulphonated products than occurs at lower temperatures, but the viscosity of the reaction liquid is lower at high temperatures, making for higher turbulence for the same power input to the pump or the same turbulence with a lower power input. A balance is drawn between the opposing factors. During the reaction, heat is evolved and the maximum temperature of the effluent reaction mixture is preferably 150° C.; the usual temperature is 25°–65° C. Generally, there is no externally applied vacuum on the loop system in which the reaction mixture and reaction liquid are kept. The loop system is usually maintained with an external pressure of at least substantially atmospheric, e.g. up to 18 atmospheres and preferably about atmospheric pressure, i.e. there is preferably no externally applied pressure or vacuum.

The liquid which is reacted with the sulphur trioxide may contain an inert liquid diluent, such as a chlorinated aliphatic hydrocarbon, e.g. carbon tetrachloride. Such a diluent may be desirable when the reaction product is so high melting or of such viscosity that the temperature needed to recycle the reaction product when liquid and give turbulent flow in the mixer would be high enough to result in undue discolouration and/or formation of other byproducts. Examples of such reaction products are those from naphthalene compounds, alkanoamides, alkoxylated derivatives thereof and alkoxylated alcohols and phenols. However, preferably the inert diluent is absent so that no step of separating the diluent after the reaction is needed and the final product is substantially the sulph(on)ated products or the main liquid contaminant is unreacted feedstock which can be separated and recycled for reuse.

After the reaction has occurred, the reaction mixture is cooled, usually to a temperature the same as the input temperature of the recycle liquid before reaction. The reaction is exothermic the heat of reaction being absorbed in the bulk of the circulating liquid as a heat sink. The cooling is preferably such as to give a maximum temperature difference of the liquid in different parts of the loop of 50° C. especially a maximum difference of 10° C. The cooling may take place in one or more stages with the reaction mixture being passed through one or more heat exchangers. Usually the portion of reaction mixture is withdrawn as reaction product after at least partial cooling of the reaction liquid and the remainder is mixed with fresh organic feedstock to compensate for the organic feedstock reacted and removed, and to bring the content of feedstock in the mixture back to the value desired for the input feed into the reaction with sulphur trioxide. The liquid with the content of organic sulph(on)atable compound restored in this fashion is then recycled for further reaction with sulphur trioxide. Alternatively but less preferred, the reaction mixture may be cooled after the portion is withdrawn, the cooling occurring before or after the fresh feedstock is added.

The portion of reaction mixture taken out of the system constitutes a fourtieth to a two thousandth of the weight of the remainder of the reaction mixture recycled, i.e. a recycle ratio of 40:1 to 2,000:1, preferably 100:1 to 1,000:1, e.g. 100:1 to 700:1 and especially 150–650:1, such as 275–550:1 e.g. 275–350:1.

The amount of the feedstock in the reaction liquid depends on the nature of the feedstock, the desired composition of the product removed from the system, and the recycle ratio.

When the feedstock is degraded by a substantial excess of sulphur trioxide and when any unreacted feedstock is difficult to separate from the sulph(on)ated product, as is true for most aliphatic feedstocks and also for example, with dodecyl benzene, the molar ratio of $SO_3$ to feedstock is usually 0.9:1 to 1.1:1, e.g. 0.9:1 to 1.05:1, preferably 0.93:1 to 1.05:1, especially 0.93:1 to 1.0:1. In these cases the molar ratio of the amount of feedstock in the reaction liquid to be contacted with $SO_3$ to the amount of sulph(on)ated derivative in that liquid is preferably 0.01:99.99 to 5:95 and especially about 0.1:99.9 to 3:97. When the feedstock to be sulphonated is not easily degraded by an excess of $SO_3$, the molar ratio of $SO_3$ to feedstock may be greater than 1:1, e.g. in the range 0.9:1 to 2:1 or if unreacted feedstock is more easily separated from the reaction product, as with lower alkyl benzenes then the molar ratio of $SO_3$ to feedstock may be 0.1:1 to 1:1 e.g. 0.5:1 to 0.95:1. Molar ratios of $SO_3$ to feedstock greater than 1.2:1 are used when disulphonation, e.g. of aromatic hydrocarbons is desired. The composition of the liquid to be reacted with $SO_3$ can vary over a wide range. When the unrected feedstock level in the product removed from the system is to be kept low so that the reaction mixture is substantially free (i.e. less than 2%) of unreacted feedstock, the molar ratio of feedstock to sulphonated derivative may be 0.01:99.99 to 10:90, preferably 0.01:99.99 to 5:95, e.g. 0.1:99.9 to 3:97. When the product is to contain a substantial amount of unreacted volatile feedstock the molar ratio of feedstock to sulphonated derivative may be 5:95 to 90:10, e.g. 15:85 to 90:10. The latter proportions may often be advantageous if the product is to be purified for removal of sulphones obtained with aromatic hydrocarbon feedstocks, because the crude product can be treated with water and the aqueous sulphonic acid layer separated from an organic layer comprising unreacted feedstock and water insoluble impurities, such as the sulphones. The sulphur trioxide:feedstock molar ratio is determined by the desired composition of the product, as well as the nature of the feedstock.

The product removed from the system can be used as such or converted to the corresponding salt by treatment with a base and/or purified to remove impurities.

Thus in the case of reaction of the aromatic compounds with sulphur trioxide in a molar ratio of less than 1:1.2 the liquid removed from the system comprises any unreacted aromatic compound and sulphonated compounds which are primarily the mono sulphonic acids of the aromatic compounds and inert liquid diluent (if used in the reaction) and also may contain small amounts of disulphonic acids, sulphuric acid and/or sulphones. When the molar ratio of sulphur trioxide to aromatic feedstock is greater than 1.2:1 the liquid removed from the system comprises sulphonated compounds which are disulphonic acids and monosulphonic acids and inert liquid diluent (if used in the reaction), and may also contain small amounts of unreacted aromatic compound, sulphuric acid and/or sulphones. The sulphonic acids may be sold as such, or after treatment with a base to form an aqueous phase comprising a solution of a sulphonate salt. The base may be an aqueous solution of an alkali metal hydroxide, carbonate or bicarbonate, e.g. sodium hydroxide or sodium carbonate or ammonia or an organic amine, such as a trialkyl amine or dialkyl amine, each with 1 to 4 carbon atoms in each alkyl group, e.g. dimethylamine or an alkylolamine, e.g. ethanolamine. Alternatively the liquid is treated with water, optionally after adding a hydrocarbon solvent e.g. benzene, toluene, xylene or paraffin to cause separation into an aqueous phase containing the sulphonic acids and an organic phase containing unreacted aromatic compound and sulphone (and the hydrocarbon added). There is no need to add further hydrocarbon if the product removed from the system contains a substantial amount of unreacted volatile aromatic compound, as mentioned above or water immiscible liquid diluent. The aqueous sulphonic acid can be used as such or converted into a salt as described above. The treatment of the crude liquid with the aqueous solution of base can also be followed by separation of the organic phase as described above. Traces of residual organic feedstock and hydrocarbons can be removed from the sulphonic acid or salt product by stripping e.g. under vacuum.

In order to minimize the production of sulphones in the sulphonation reaction, when the feedstock is benzene or benzene substituted by at least one alkyl chain of 1–5 carbon atoms, it is preferred to carry out the reaction in the presence of a sulphone inhibitor.

The sulphone inhibitor is usually added with the feeds if it is soluble therein, but otherwise it is added separately to the reaction liquid usually before the addition of the sulphur trioxide. Amount of inhibitor of up to 10% (by weight based on the weight of the sulfonated product) may be used, e.g. up to 5%, preferably 0.5–5% especially 1–5%. The inhibitors may be oxygenated compounds, nitrogenous compounds or metal salts. The class of oxygenated compounds includes those described in our British Patent Specification No. 1306226 such as cyclic ethers, e.g. of 4–8 carbon atoms such as dioxan or tetrahydrofuran, dialkyl ethers, e.g. of 1–4 carbon atoms in each alkyl group such as diethyl ether, dialkyl ketones, e.g. of 3–7 carbon atoms such as acetone and methyl ethyl ketone, cycloaliphatic ketones such as cyclo-hexanone, carboxylic acids, e.g. of 2–6 carbon atoms such as acetic or propionic acids, esters of these carboxylic acids, e.g. with alkanols of 1 to 6 carbon atoms such as ethyl acetate, and anhydrides of those carboxylic acids such as acetic anhydride; acetic acid and acetic anhydride are preferred. The class of nitrogenous compounds includes those described in our British Patent Specification No. 1304514 and includes mono amines e.g. of formula $R_3N$ where each R, which may be the same or different, is hydrogen, alkyl e.g. of 1 to 6 carbon atoms, cycloalkyl, e.g. of 5–7 carbon atoms or aryl (preferably aromatic hydrocarbyl), e.g. of 6–12 carbon atoms, such as ammonia, di and tri alkyl amines such as triethyl amine and diisopropylamine, primary aromatic and cycloalkyl amines such as aniline and cyclohexylamine; diamines and triamines, e.g. alkylene diamines of 2–6 carbon atoms such as ethylene diamine and alkylene triamines of 4–10 carbon atoms such as diethylene triamine: heterocyclic amines such as pyridine, quinoline and isoquinoline; carboxylic acid amides e.g. the amide from any primary or secondary amine mentioned above preferably ammonia or dimethyl amine and a carboxylic acid of 1 to 4 carbon atoms such as carbonic, formic and acetic acids, preferably urea, dimethyl formamide and dimethyl acetamide; amine salts, where the amine part can be based on any of the amines mentioned above, e.g. ammonium, and the acid part is from an inorganic acid such as hydrochloric, sulphuric or phosphoric acid, or an organic, sulphonic or carboxylic acid such as aromatic hydrocarbyl or alkyl sulphonic acids such as xylene-, toluene-, benzene-, or methane sulphonic acids. The metal salts includes alkali metal salts of organic or inorganic acids, which are the alkali metal salt equivalents of the amine salts mentioned above.

When the sulphonated aromatic product is wanted in its acid form, the inhibitor is preferably an oxygenated compound, e.g. acetic acid or acetic anhydride because the other inhibitors introduce often undesirable compounds into the acid, e.g. ammonium salts. When the sulphonated aromatic product is wanted in its salt form, the presence of ammonium salts or production of ammonia as byproducts from, e.g. urea is of no consequence because the neutralization of the free acid product liberates the amine or ammonia, which can be separated from the salt.

The feedstock or the sulphone inhibitor (if the latter is not added with the feedstock) may be mixed with up to 300% (by weight of inhibitor), preferably 20–170% of water or the water may be added separately to the reaction liquid. The water appears to act as an auxiliary sulphone inhibitor but may result in a higher percentage of free sulphuric acid in the reaction product, which may be desirable in certain applications. Water added alone is a poor sulphone inhibitor and increases the content of free sulphuric acid in the reaction product considerably. Examples of useful combinations of inhibitor and water are water and carboxylic acids, ester or anhydrides, e.g. water and acetic acid, acetic anhydride or ethyl acetate.

When the organic feedstock sulphated is a fatty alcohol, the reaction mixture removed from the system comprises unreacted alcohol and the desired mono alkyl sulphate (and inert diluent if present) together sometimes with the di alkyl sulphate ester. The mixture is usually treated with an aqueous solution of a base, e.g. one as described above to form an aqueous phase comprising an aqueous solution of a sulphate salt. The amount of base is at least sufficient to neutralize the reaction product. Similar operations may be carried out when the feedstock is any of the other sulphatable compounds.

The sulph(on)ated products of our invention can be treated by any of the known techniques used to produce saleable materials. For example, in the case of the sulphonation of olefins having 8–20 carbon atoms it is necessary to include a process step which results in the hydrolysis of the sultones formed in the reaction. Another example is that in the case of the sulphonation of dodecyl benzene it may be desirable to add small amounts of water to the sulphonic acid product in order to prevent the colour of the sulphonic acid darkening on storage and to prevent pH drift of salts produced from it. This procedure is disclosed in British Patent Specification No. 804349. If desired one of the process steps in the treatment of the products of the invention can be bleaching by any suitable means.

In a most preferred process, the sulph(on)ation is carried out in a recycle loop reactor having in the direction of flow of reaction liquid and mixture, an inlet for feedstock, an orifice plate mixer an inlet for sulphur trioxide preferably in the form of a tube surrounded by reaction liquid upstream of the orifice, the tube ending in the orifice or passing through the orifice and emitting the sulphur tri oxide downstream of the orifice, the sulphur trioxide being discharged in a coaxial direction with respect to the bulk direction of flow of the liquid, a pump, a heat exchanger as cooler and an outlet for said reaction mixture, the sulph(on)ation reaction being carried out with undiluted gaseous sulphur trioxide and a reaction liquid free of inert diluent at a temperature of 20°–80° C. under substantially no externally applied pressure or vacuum, the Reynolds Number at the point of mixing being 3,000–10,000, e.g. 3000–4500 the recycle weight ratio of the reaction mixture removed to the recycled remainder being 275–550:1 preferably 275–350:1 and, when the feedstock is benzene or an alkyl benzene, the reaction liquid also contains a sulphone inhibitor in amount of 1–5% by weight of feedstock.

The invention may be illustrated with reference to the accompanying drawings, in which FIG. 1 represents a flow diagram of a preferred process and FIG. 2 a flow diagram of an alternative but less preferred process.

Figure 2:
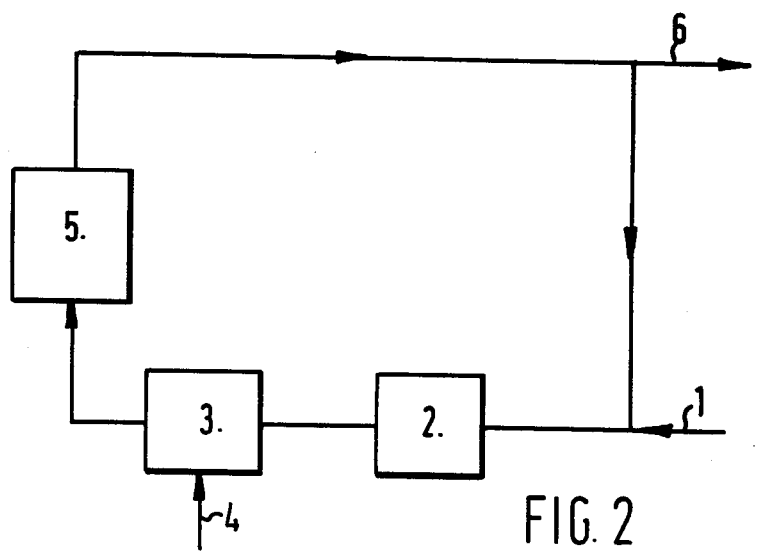

In FIGS. 1 and 2 of the drawings the loop has an input line 1, a pump 2, turbulent flow mixer 3, an input line 4 to mixer 3, a heat exchanger 5, and an output line 6.

In the operation of FIG. 1 the mixture of unreacted organic feedstock and sulph(on)ated organic feedstock (referred to hereafter as a "heel") is circulated round the loop by pump 2. Fresh organic feed stock is passed into the loop from line 1 and the mixture of it and the heel is rendered turbulent, so that the mixthre is turbulent at the point in mixer 3 where sulphur trioxide enters the loop from line 4, the reaction mixture produced is drawn through pump 2 and pumped further round the loop through the heat exchanger 5; a very small portion of the reaction mixture is removed through line 6 and the remainder is recycled for contact with fresh organic feedstock from line 1. Alternatively the remainder of the small portion of the reaction mixture may be removed before passage through the heat exchanger.

The operation of FIG. 2 is similar, except that the pump 2 and mixer 3 are transposed.

The mixer is one which imparts turbulence to the liquid flowing through it at the point of introduction of the sulphur trioxide and thereafter in the reaction zone. Various types of mixer have been described above.

The invention is illustrated by the Examples set out in the following Tables.

For Examples 1 and 2, the apparatus was as shown in FIG. 2, while for Examples 3–8, that of FIG. 1 was used. The Table gives the approximate Reynolds Number at the point of mixing the $SO_3$ and the reaction liquid, the Number quoted being calculated on the assumption that there is no gas phase present. The "Silverson" mixer was an in line mixer emulsifier, ½ horsepower model, and in Examples 1–3 was operated with its rotor turning and in Example 4 with no power to the rotor with the end of the $SO_3$ inlet tube in the orifice separating the rotor chamber from the base chamber into which the feedstok and recycle are passed. The "tunable" orifice plate mixer in Examples 5–8 was an orifice plate mixer with a 0.5 inch orifice and an inlet tube for the $SO_3$, which was surrounded by the reaction liquid upstream of the orifice and the position of the end of the tube was adjustable to be upstream, downstream or within the orifice, discharging the $SO_3$ in a coaxial direction of flow with respect to the bulk direction of flow of the liquid, in these Examples the end of the tube was within the orifice.

The recycle ratio quoted is the weight ratio of the circulation rate to the rate of feeding the feedstock and $SO_3$ into the loop, the rate of input feed is the same as the rate of off take.

For Examples 1–7, the reaction product taken from the loop at outlet 6 was analysed for total acidity (by titration with alkali, and expressed as % sulphuric acid), % free sulphuric acid, % sulphone, % free hydrocarbon and % disulphonic acids. The colour quoted was ten times the reading measured using an Eel Colorimeter with a Blue 303 filter on an aqueous solution of the reaction product, obtained by adding water to the reaction product to give a 65% by weight aqueous solution of sulphonic acid and separating unreacted hydrocarbon and any precipitate of sulphone.

For Example 8, the alcohol sulphated was a mixture of fatty alcohols in which $C_{12}$ and $C_{14}$ alcohols predominated, the mixture being that sold under the Trade Name "Laurex NC". The reaction product was neutralized with aqueous sodium hydroxide to yield a 28% aqueous solution, whose colour was measured as before. The neutralized reaction product was also analyzed for total surface active matter, sodium sulphare and free fatty matter (by ether extraction of the neutralized product).

| Ex. | Feedstock | Feedstock Feed-rate (lbs/hr) | $SO_3$ Physical State | $SO_3$ Feed-rate (lbs/hr) | Molar Ratio $SO_3$: Feedstock | Sulphone Inhibitor added with Feedstock (Wt. % of feedstok) | Mixer | Approx. Reynolds No. | Circulation Rate Imp. Gal/hr | approx. lbs/hr | Temperature °C. of Reaction Liquid in loop | Recycl Ratio |
|---|---|---|---|---|---|---|---|---|---|---|---|---|
| 1 | Toluene | 10.0 | Liquid | 9.0 | 1:0.97 | Ethyl acetate (1.75%) | Silverson (Running) | 1,330 | 700 | 9100 | 27–32 | 480 |
| 2 | Toluene | 9.4 | Vapour | 8.2 | 1:1 | Ethyl acetate (1.75%) | Silverson (Running) | 1,330 | 700 | 9100 | 29–33 | 515 |
| 3 | Xylene | 20.9 | Vapour | 9.0 | 1:1.75 | Ethyl acetate (1.75%) | Silverson (Running) | 1,896 | 1000 | 10000 | 21–23 | 335 |
| 4 | Toluene | 24.0 | Vapour | 18.0 | 1:1.16 | Ethyl acetate (1.75%) | Silverson (Switched off) | 2,300 | 1000 | 12500 | 31–33 | 298 |
| 5 | Xylene | 23.8 | Vapour | 18.0 | 1:1 | Ethyl acetate (1.75%) | Orifice (Tunable) | 3,600 | 1000 | 13000 | 45–50 | 310 |
| 6 | Xylene | 23.8 | Vapour | 18.0 | 1:1 | Dimethyl Formamide (1.75%) | Orifice (Tunable) | 4,110 | 1000 | 13000 | 51–55 | 310 |
| 7 | Xylene | 25.0 | Vapour | 18.0 | 1:1.05 | Acetic anhydride (1.75%) | Orifice (Tunable) | 4,110 | 1000 | 13000 | 48–53 | 310 |
| 8 | "Laurex NC" Alcohol | 25.0 | Vapour | 10.0 | 1:1.03 | None | Orifice (Tunable) | 3,200 | 1000 | 10000 | 28–30 | 286 |

In the cases of Ex. 1–3, the Reynolds No. quoted is a minimum figure calculated on the assumption that the rotor in the Silverson mixer is not moving. In fact significant turbulence results from the movement of the rotor, so that the reaction liquid is in a state of turbulent flow at the point of entry of the sulphur trioxide and downstream.

PRODUCT ANALYSIS

| Example | Total Acidity (as sulphuric acid %) | Sulphuric Acid (%) | Sulphones (%) | Free Hydrocarbon (%) | Disulphonic Acid (%) | Colour (Eel B) |
|---|---|---|---|---|---|---|
| 1 | 28.9 | 2.1 | 3.9 | 0.5 | 4.4 | 18 |
| 2 | 28.1 | 1.4 | 4.3 | 0.6 | 1.1 | 13 |
| 3 | 19.7 | 1.6 | 5.3 | 30.0 | 0.9 | 7 |
| 4 | 26.5 | 2.0 | 4.7 | 6.6 | 0.2 | 8 |
| 5 | 27.8 | 2.2 | 3.0 | Less than 0.1 | 0.6 | 2 |
| 6 | 26.1 | 1.3 | 1.8 | 1.1 | 1.5 | 4 |
| 7 | 25.2 | 0.7 | 3.8 | 4.7 | 0.5 | 2 |

Surface Active Matter (%)   Sodium sulphate   Free Fatty

| | | PRODUCT ANALYSIS | | |
|---|---|---|---|---|
| Example | by weight | (%) | Matter % | Colour (Eel B) |
| 8 | 27.0 | 0.7 | 0.5 | 9 |

We claim:

1. A continuous cyclic process for sulph(on)ating a sulph(on)atable organic feedstock by reacting said feedstock with sulphur trioxide comprising forming a reactant liquid substantially free of inert diluent and comprising the organic feedstock and its sulph(on)ation derivative which has been recycled, passing said reactant liquid through a static mixer without any moving parts and also passing undiluted liquid or gaseous sulphur trioxide through said static mixer to contact said reactant liquid and form a reaction mixture, said reactant liquid being in a condition of turbulent flow at the point of contact of the sulphur trioxide and said reactant liquid and thereafter in the zone of reaction of sulphur trioxide and said reactant liquid, removing a portion of the reaction mixture as sulph(on)ated product, the weight ratio of reaction mixture removed as said product to the remainder of the reaction mixture being in the range of about 1:40 to 1:2000, cooling said reaction mixture before and/or after removing said portion of the reaction mixture as said product, recycling said remainder of said reaction mixture and adding additional organic feedstock to said remainder of said reaction mixture to compensate for that removed as said product to form said reactant liquid, and maintaining the temperature of said reactant liquid and said reaction mixture throughout the process within a maximum temperature differential of 10° C. and maintaining said reactant liquid and reaction mixture in said cyclic process under no externally applied vacuum.

2. A process according to claim 1 wherein the apparent Reynolds Number of said reactant liquid at the point of contact with the sulphur tri oxide is 3000–18,000.

3. A process according to claim 2 wherein the apparent Reynolds Number of said reactant liquid at the point of contact with the sulphur trioxide is 3000–10,000.

4. A process according to claim 1 wherein the weight ratio of the reaction mixture removed to the recycled remainder is 1:100 to 1:600.

5. A process according to claim 1 wherein the sulphur trioxide is in gaseous form.

6. A process according to claim 1 wherein said static mixer is in an orifice plate mixer, a jet mixer, a venturi mixer, or a Kenic mixer.

7. A process according to claim 1 wherein the mixer is an orifice plate mixer.

8. A process according to claim 1 wherein said reactant liquid and sulphur trioxide are contacted at a temperature of 0°–80° C.

9. A process according to claim 1 wherein the molar ratio of sulphur trioxide to feedstock is such that the reaction mixture is substantially free of unreacted feedstock.

10. A process according to claim 1 which is carried out in a recycle loop reactor having in the direction of flow of said reactant liquid and reaction mixture, an inlet for feedstock, a mixer giving turbulent flow, a pump, a heat exchanger as cooler and an outlet for reaction mixture.

11. A process according to claim 1 wherein the feedstock is benzene, or alkyl benzene having 1-3 alkyl groups each of 1 to 3 carbon atoms, a fatty alcohol of 8-20 carbon atoms, or olefins of 8-20 carbon atoms.

12. A process according to claim 1 wherein the feedstock is toluene or xylene.

13. A process according to claim 1 in which the feed stock is benzene or an alkyl benzene, wherein said reactant liquid also comprises a sulphone inhibitor in amount of up to 10% by weight based on the weight of the feedstock.

14. A process according to claim 13 wherein the inhibitor is acetic acid, acetic anhydride or an alkyl acetate with 1-6 carbon atoms in the alkyl group.

15. A process according to claim 13 wherein water is added to said reactant liquid in amount of up to 300% by weight of the inhibitor.

16. A process according to claim 13 wherein the inhibitor is an amine or ammonium salt, amide or urea.

17. A process according to claim 1, wherein the portion of the sulphonated reaction mixture withdrawn is treated with water to give an aqueous phase comprising an aqueous solution of a sulphonic acid.

18. A process according to claim 1 wherein the portion of the sulphonated or sulphated reaction mixture is treated with an aqueous solution of a base to give an aqueous phase comprising a solution of a sulphonate or sulphate salt.

19. A method according to claim 11 wherein the sulph(on)ation is carried out in a recycle loop reactor having in the direction of flow of said reactant liquid and reaction mixture, and inlet for feedstock, a mixer comprising an orifice plate, an inlet for sulphur trioxide, a pump, a heat exchanger as cooler and an outlet for said reaction mixture, the sulph(on)ation being carried out with undiluated gaseous sulphur trioxide and a reaction liquid free of inert diluent at a temperature of 20-80° C. under substantially no externally applied pressure or vacuum, the Reynolds Number at the point of mixing being 3000–10,000, the weight ratio of the reaction mixture removed to the recycled remainder being between 1:150 and 1:550 and, when the feedstock is benzene or an alkyl benzene, the reaction liquid also contains a sulphone inhibitor in an amount of 1-5% by weight of feedstock.

* * * * *

UNITED STATES PATENT AND TRADEMARK OFFICE
CERTIFICATE OF CORRECTION

PATENT NO. : 4,226,796
DATED : October 7, 1980
INVENTOR(S) : BRIAN J. AKRED et al It is certified that error appears in the above—identified patent and that said Letters Patent is hereby corrected as shown below:

Column 1, line 16: " "sulph(on)atable ⇌ " should read --"sulph(on)atable"--.

Column 4, line 36: "10°-60" should read --20°-60°--.

Column 6, line 59: "feeds" should read --feedstock--.

Column 6, line 62: "Amound" should read --Amounts--.

Signed and Sealed this

First Day of June 1982

[SEAL]

Attest:

GERALD J. MOSSINGHOFF

Attesting Officer    Commissioner of Patents and Trademarks